(12) United States Patent
Akle et al.

(10) Patent No.: US 8,617,520 B2
(45) Date of Patent: Dec. 31, 2013

(54) CANCER THERAPY

(75) Inventors: Charles Akle, London (GB); Satvinder Mudan, London (GB); John Grange, London (GB)

(73) Assignee: Immodulon Therapeutics Limited, London (GB)

( * ) Notice: Subject to any disclaimer, the term of this patent is extended or adjusted under 35 U.S.C. 154(b) by 0 days.

(21) Appl. No.: 13/396,866

(22) Filed: Feb. 15, 2012

(65) Prior Publication Data

US 2013/0209517 A1    Aug. 15, 2013

(51) Int. Cl.
*A61K 49/00*    (2006.01)
*A61K 39/04*    (2006.01)
*A61K 39/35*    (2006.01)

(52) U.S. Cl.
USPC ....... 424/9.1; 424/9.2; 424/184.1; 424/248.1; 424/278.1

(58) Field of Classification Search
USPC ............... 424/9.1, 9.2, 184.1, 248.1, 278.1
See application file for complete search history.

(56) References Cited

PUBLICATIONS

Apetoh, L et al., "Cancer is not just a disease of a tissue: it is a host disease. How to reactivate host defense against tumours using conventional therapies of cancer?" *Annales d'endocrinologie* (Paris), 2008, 69:151-152, [abstract].

Apetoh, L et al., "Molecular Interactions between Dying Tumour Cells and the Innate Immune System Determine the Efficacy of Conventional Anticancer Therapies" *Cancer Research*, 2008, 68:4026-30.

Dunn, GP et al., "The three Es of cancer immunoediting" *Annual Review of Immunology*, 2004, 22:329-360, [abstract].

Dvorak, HF, "Tumours: wounds that do not heal. Similarities between tumour stroma generation and wound healing." *New England Journal of Medicine*, 1986, 315:1650-1659, [abstract].

Ladoire, S et al., "Pathologic Complete Response to Neoadjuvant Chemotherapy of Breast Carcinoma is Associated with the Disappearance of Tumour-Infiltrating Foxp3+ Regulatory T Cells" *Clinical Cancer Research*, 2008, 14:2413-2420.

Locher, C et al., "Desirable cell death during anticancer chemotherapy" *Annals of the New York Academy of Sciences*, 2010, 1209:99-108.

Ménard, C et al., "Cancer chemotherapy: not only a direct cytotoxic effect, but also an adjuvant for antitumor immunity" *Cancer Immunology, Immunotherapy*, 2008, 57:1579-1587.

Tesniere, A et al., "Molecular characteristics of immunogenic cancer cell death" *Cell Death & Differentiation*, 2008, 15:3-12.

Tesniere, A et al., "Immunogenic cancer cell death: a key-lock paradigm" *Current Opinion in Immunology*, 2008, 20:504-511.

Vakkila, J and Lotze, MT, "Inflammation and necrosis promote tumour growth" *Nature Reviews Immunology*, 2004, 4:641-648.

Zeh, HJ and Lotze, MT, "Addicted to death: invasive cancer and the immune response to unscheduled cell death" *Journal of Immunotherapy*, 2005, 28:1-9, [abstract].

Zitvogel, L et al., "Immune response against dying tumor cells" *Advances in Immunology*, 2004, 84:131-179, [abstract].

Zitvogel, L et al., "The anticancer immune response: indispensable for therapeutics success?" *Journal of Clinical Investigation*, 2008, 118:1991-2001.

*Primary Examiner* — Rodney P. Swartz

(74) *Attorney, Agent, or Firm* — Saliwanchik, Lloyd & Eisenschenk

(57) ABSTRACT

The present invention relates to a method of preventing, treating or inhibiting the development of tumors or metastases in a subject and to an immunomodulator for use in such therapy, in combination with a chemotherapeutic agent. An aspect the present invention is a method of preventing, treating, reducing, inhibiting and/or controlling the formation or establishment of metastasis of a primary neoplasia, tumor or cancer at one or more sites distinct from a primary neoplasia, tumor or cancer, in a subject intended to undergo chemotherapy, wherein the method comprises administering to the subject, a therapeutically effective amount of an antimetabolite pyrimidine analogue and an immunomodulator.

11 Claims, 2 Drawing Sheets

CANCER THERAPY

FIELD OF THE INVENTION

The present invention relates to the field of cancer therapy. In particular, the present invention relates to a method of preventing, treating or inhibiting the development of tumours or metastases in a subject and to an immunomodulator for use in such therapy, in combination with a chemotherapeutic agent.

BACKGROUND OF THE INVENTION

In recent years there has been a growing realization that immune responses play a central role in cancer biology by eliminating many tumours at a very early stage and keeping those that avoid total elimination in a state of equilibrium, sometimes for many years (Dunn et al., *Annu Rev Immunol* 2004; 22:329-360). The eventual escape from this equilibrium phase with clinical manifestation of the disease is associated with dysregulated immune responses, manifesting, for example, as chronic inflammation or immune tolerance. The strong and increasing evidence that the immune system is critically involved in the development, structural nature and progression of cancer has led to renewed interest in immunotherapeutic strategies for treatment of this class of diseases. To date, most attempts to develop such strategies have been based on the use of antigens derived from the patient's own tumour or from tumour cell lines and the transfer of ex-vivo expanded populations of tumour antigen-specific cytotoxic cells and antigen-presenting cells.

Cancer has been associated with inflammation since 1863, when Rudolf Virchow discovered leucocytes in neoplastic tissues and so made the first connection between inflammation and cancer (Balkwill et al., *Lancet* 2001; 357:539-545). Since then, chronic inflammation has been deemed to be a risk factor for cancer. These reports demonstrate that an inflammatory environment supports tumour development and is consistent with that observed at tumour sites. However, the relationship of cancer with inflammation is not limited to the onset of the disease due to chronic inflammation. Schwartsburd (*Cancer and Metastasis reviews* 2003; 22:95-102) proposed that chronic inflammation occurs due to tumour environment stress and that this generates a shield from the immune system. It has been recently demonstrated that the tumour microenvironment resembles an inflammation site, with significant support for tumour progression, through chemokines, cytokines, lymphocytes and macrophages which contribute to both the neovascularisation and vasal dilation for increased blood flow, the immunosuppression associated with the malignant disease, and tumour metastasis. Furthermore, this inflammation-site tumour-generated microenvironment, apart from its significant role in protection from the immune system and promotion of cancer progression, has an adverse effect on the success of current cancer treatments. Indeed, it has been found that the inflammatory response in cancer can compromise the pharmacodynamics of chemotherapeutic agents (Slaviero et al., *Lancet Oncol* 2003; 4:224-32).

Moreover, metastatic cancer cells leave the tumour as microcolonies, containing lymphocytes and platelets as well as tumour cells. Inflammation continues to play a role at metastatic sites by creating a cytokine milieu conducive to tumour growth.

Immune homeostasis consists of a tightly regulated interplay of pro- and anti-inflammatory signals. For example, loss of the anti-inflammatory signals leads to chronic inflammation and proliferative signalling. Interestingly, cytokines that both promote and suppress proliferation of the tumour cells are produced at the tumour site. As in the case of cancer initiation, it is the imbalance between the effects of these various processes that results in tumour promotion.

It is believed that, to treat cancer, the most effective type of immune response is of a Type 1, which favours the induction of CD4+Th1 cellular responses, and of CD8+CTL responses. In the context of cancer vaccines, many immune stimulants are used, which promote the development of Th1 responses and are thought to inhibit the production of a Th2 response. For example, BCG (bacillus Calmette-Guerin) an attenuated strain of *M. bovis* developed as a vaccine against *M. tuberculosis* infection is also used for treatment of various other conditions, such as bladder carcinoma and cutaneous melanoma. Intravesical instillation of BCG for superficial transitional cell carcinoma of the bladder is currently considered a first-line treatment for this disease. Although serious complications with intravesical BCG are uncommon, these can occur in individuals and can range from local symptoms to hepatitis, pneumonitis, sepsis, and death. SRL-172 is a heat-killed preparation of *Mycobacterium vaccae*, a member of the same genus as bacille Calmette-Guerin (BCG) but with additional immunological properties, as it induces both immuno-regulation and Type 1 enhancing effects.

To date, a major barrier to attempts to develop effective immunotherapy for cancer has been an inability to break immunosuppression at the cancer site and restore normal networks of immune reactivity. The physiological approach of immunotherapy is to normalize the immune reactivity so that the endogenous tumour antigens would be recognized and effective cytolytic responses would be developed against cells bearing these antigens.

Anti-cancer immune responses accompanying the action of chemo- and radiotherapy have been reviewed in detail and show that such responses are indispensible to therapeutic success by eliminating residual cancer cells and maintaining micrometastases in a state of dormancy (Zitvogel et al., *J Clin Invest* 2008; 118:1991-2001). However, this reference makes it clear that there is no simple immunotherapeutic strategy available for consistently enhancing such immune responses. Likewise, it has been suggested that radiofrequency ablation of tumours, mainly hepatic, could, by providing an accessible and immunogenic source of tumour antigens, synergise with active immunotherapy, if such immunotherapy were developed (Fagnoni et al., *Front Biosci* 2008; 13:369-381).

There is evidence that therapeutic procedures that induce certain forms of cancer cell death also lead to surface expression or release of tumour antigens. There are three main types of cell death (Tesniere et al., *Cell Death Differ* 2008; 15:3-12): apoptosis (type 1), autophagy (type 2) and necrosis (type 3). Apoptosis, or programmed cell death, is a common and regular occurring phenomenon essential for tissue remodelling, especially in utero but also throughout life. It is characterized by DNA fragmentation in the nucleus and condensation of the cytoplasm to form 'apoptotic bodies' which are engulfed and digested by phagocytic cells. In autophagy, cell organelles and cytoplasm are sequestered in vacuoles which are extruded from the cell. Although this provides a means of survival for cells in adverse nutritional conditions or other stressful situations, excess autophagy results in cell death. Necrosis is a 'cruder' process characterized by damage to intracellular organelles and cell swelling, resulting in rupture of the cell membrane and release of intracellular material.

It has widely been held that apoptosis is immunologically 'silent', as would be expected from its physiological role and by the finding that local inflammation is suppressed by the release of anti-inflammatory mediators. More recently it has been suggested that there are different forms of apoptosis and some are immunogenic (Zitvogel et al., *Adv Immunol* 2004; 84: 131-179). The relationship of autophagy to immunogenicity is poorly understood but necrosis certainly releases many antigens, although in progressive cancers, such necrosis might also enhance the chronic inflammation that favours tumour growth (Vakkila et al., *Nat Rev Immunol* 2004; 4: 641-648; Zeh et al., *J Immunother* 2005; 28:1-9). In this sense, a cancer resembles a chronically inflamed wound that does not heal (Dvorak. *N Engl J Med* 1986; 315:1650-1659).

Efforts have been made in the art to provide combined ablative and chemotherapies for the treatment of tumours. WO2000064476 and US20050187207 disclose the use of an immunoadjuvant in combination with photodynamic therapy for the treatment of metastatic tumours. These documents disclose that the immunoadjuvant comprises mycobacterial cell wall skeletons and de-3-O-acylated lipid A and is administered by injection into the tumour. Castano et al. (*Nat Rev Cancers* 2006; 6:535), Korbelik et al. (*J Photochem and Photobiol* 1998; 44:151) and Korbelik et al. (*J Photochem and Photobiol*, 2001; 73:403) also disclose the treatment of tumours using a combination of photodynamic therapy and the administration of mycobacterial cell wall extract as an immunoadjuvant. Mycobacterial cell walls contain compounds such as trehalose dimycolate and muramyl dipeptide which are known immunostimulators. The mycobacterial cell wall extracts used in the prior art combination therapies also elicit pro-inflammatory cytokines, reactive nitrogen species and recruit leukocytes which are associated with pathology including weight loss due to TNF-α, mediated cachexia, with associated lipidemia, hypoglycaemia and peritonitis with ischemic and hemorrhagic lesions in the GI tract. The prior art combination therapies may therefore exacerbate the inflammatory response and have severe side effects.

An aim of the present invention is to solve the problems associated with the combination therapies for tumours observed in the prior art and, specifically, to provide a treatment for secondary cancers formed by metastasis of a primary cancer away from the site of the primary cancer.

SUMMARY OF THE INVENTION

The present invention overcomes the deficiency in the prior art by providing a safe, better tolerated and effective method for treating and/or preventing cancer by employing chemotherapeutic agents which act synergistically with immunotherapy. Chemotherapeutic agents generate beneficial therapeutic responses, in part at least by interfering with tumour cell proliferation. The present invention therefore provides a combination therapy of a chemotherapeutic agent with a specific type of immunotherapy. The inventors have found that the combination of both therapies is synergistic beyond simple additive effects of each therapy used individually. Surprisingly, the present combination therapy results in a balanced immunoregulatory and Type 1 enhancing effect, with a reduction of inappropriate Th2-type responses and the inflammation generally associated with the prior art combination therapies. This multi-faceted profile of action cannot be achieved by intervention of a single pathway and so results in a more controlled response compared to the prior art.

Therefore, in one aspect the present invention is a method of preventing, treating, reducing, inhibiting and/or controlling the formation or establishment of metastasis of a primary neoplasia, tumour or cancer at one or more sites distinct from a primary neoplasia, tumour or cancer, in a subject intended to undergo chemotherapy, wherein said method comprises simultaneously, separately or sequentially administering to the subject, a therapeutically effective amount of (i) an antimetabolite pyrimidine analogue, and (ii) an immunomodulator.

The present invention therefore provides a combination therapy of chemotherapy together with a specific type of immunotherapy. The inventors have found that the combination of both therapies is synergistic beyond simple additive effects of each therapy used individually.

DESCRIPTION OF THE DRAWINGS

The invention is described with reference to the following drawings, in which.

DETAILED DESCRIPTION OF THE INVENTION

Figure 1:
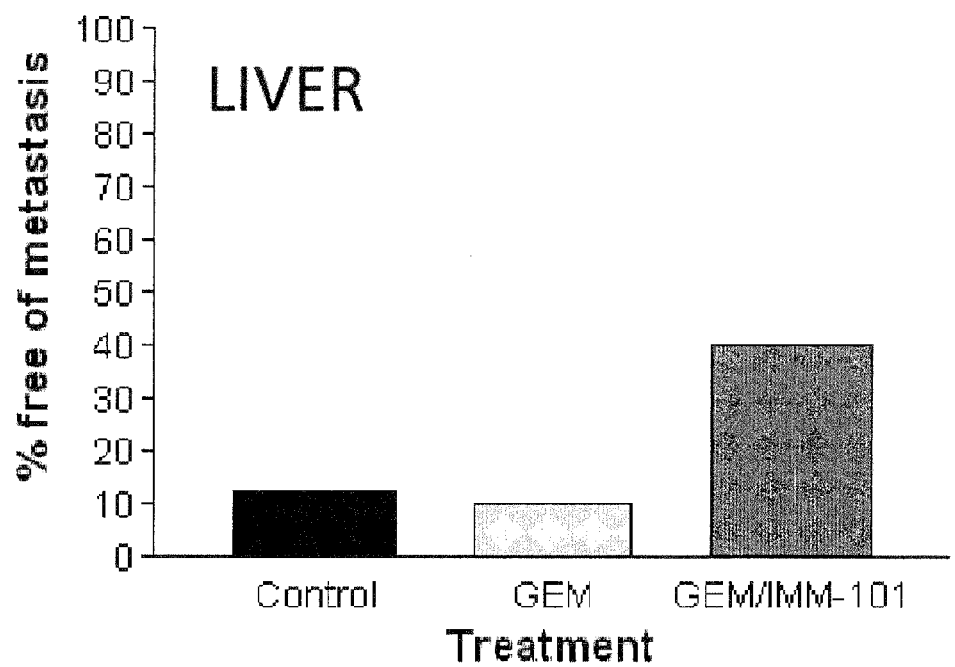
FIG. 1 shows the effect of IMM-101 with or without co-administration of gemcitabine, on the spread of liver metastases.

An immunomodulator, as defined according to the present invention, is a component which stimulates Type 1 response and down regulates Th2 responses and which restores the healthy balance of the immune system.

The terms "tumour," "cancer" and "neoplasia" are used interchangeably and refer to a cell or population of cells whose growth, proliferation or survival is greater than growth, proliferation or survival of a normal counterpart cell, e.g. a cell proliferative or differentiative disorder. Typically, the growth is uncontrolled. The term "malignancy" refers to invasion of nearby tissue. The term "metastasis" refers to spread or dissemination of a tumour, cancer or neoplasia to other sites, locations or regions within the subject, in which the sites, locations or regions are distinct from the primary tumour or cancer.

The term "chemotherapy" and "chemotherapeutic agent" are used interchangeably and refer to the use or administration of antimetabolite pyrimidine analogues in the method of the invention, selected from; thymidylate synthase inhibitors such as capecitabine, Tegafur, Carmofur, floxuridine; DNA polymerase inhibitors such as cytarabine, fazarabine, sapacitabine, or valopicitabine; ribonucleotide reductase inhibitors such as gemcitabine; hypomethylating agents, such as azacitidine, decitabine or a pharmaceutically acceptable salt, solvate, hydrate, stereoisomer, clathrate, prodrug or combinations thereof.

"Simultaneous" administration, as defined herein, includes the administration of the immunomodulator and agent or procedure comprising chemotherapy within about 2 hours or about 1 hour or less of each other, even more preferably at the same time.

"Separate" administration, as defined herein, includes the administration of the immunomodulator and agent or procedure comprising chemotherapy more than about 12 hours, or about 8 hours, or about 6 hours or about 4 hours or about 2 hours apart.

"Sequential" administration, as defined herein, includes the administration of the immunomodulator and chemotherapeutic agent each in multiple aliquots and/or doses and/or on separate occasions. Preferably the immunomodulator is administered before and continued to be administered to the patient after administration of the chemotherapeutic agent. More preferably, the immunomodulator is continued to be applied to the patient after treatment for regression of the tumour.

In one aspect of the present invention the immunomodulator comprises heat-killed *Mycobacterium*. Preferred mycobacterial species for use in the present invention include *M. vaccae, M. thermoresistibile, M. flavescens, M. duvalii, M. phlei, M. obuense, M. parafortuitum, M. sphagni, M. aichiense, M. rhodesiae, M. neoaurum, M. chubuense, M. tokaiense, M. komossense, M. aurum, M. w, M. tuberculosis, M. microti; M. africanum; M. kansasii, M. marinum; M. simiae; M. gastri; M. nonchromogenicum; M. terrae; M. triviale; M. gordonae; M. scrofulaceum; M. paraffinicum; M. intracellulare; M. avium; M. xenopi; M. ulcerans; M. diernhoferi, M. smegmatis; M. thamnopheos; M. flavescens; M. fortuitum; M. peregrinum; M. chelonei; M. paratuberculosis; M. leprae; M. lepraemurium* and combinations thereof.

Preferably, the heat-killed *Mycobacterium* is non-pathogenic. The non-pathogenic heat-killed *Mycobacterium* is selected from *M. vaccae, M. obuense, M. parafortuitum, M. aurum, M. w, M. phlei* and combinations thereof. More preferably the non-pathogenic heat-killed *Mycobacterium* is a rough variant. The amount of immunomodulator administered to the patient is sufficient to elicit a protective immune response in the patient such that the patient's immune system is able to mount an effective immune response to tumour cell antigens following tumour cell ablation, or immunogenic cell death. In certain embodiments of the invention, it is preferable that particular a dosage of immunomodulator be administered to a subject. Thus, in certain embodiments of the invention, there is provided a containment means comprising the effective amount of heat-killed *Mycobacterium* for use in the present invention, which typically may be from $10^3$ to $10^{11}$ organisms, preferably from $10^4$ to $10^{10}$ organisms, more preferably from $10^6$ to $10^{10}$ organisms, and even more preferably from $10^6$ to $10^9$ organisms. The effective amount of heat-killed *Mycobacterium* for use in the present invention may be from $10^3$ to $10^{11}$ organisms, preferably from $10^4$ to $10^{10}$ organisms, more preferably from $10^6$ to $10^{10}$ organisms, and even more preferably from $10^6$ to $10^9$ organisms. Most preferably the amount of heat-killed *Mycobacterium* for use in the present invention is from $10^7$ to $10^9$ cells or organisms. Typically, the composition according to the present invention may be administered at a dose of from $10^8$ to $10^9$ cells for human and animal use. Alternatively the dose is from 0.01 mg to 1 mg or 0.1 mg to 1 mg organisms presented as either a suspension or dry preparation.

*M. vaccae* has the ability to modulate immune responses. Its Type 1 adjuvant property is unaffected by heat-killing, whereas other mycobacteria, such as BCG, have little Type 1 adjuvant effect when dead. *M. vaccae* also downregulates pre-existing Th2 responses in a manner that appears to be independent of its ability to enhance Th1 responses. This effect has now been attributed to induction of CD4+ CD45RB$^{low}$ regulatory T-cells that in an experimental model of pulmonary allergic inflammation can suppress allergic inflammation and airway hyper-reactivity when transferred to allergic recipients. *M. obuense* also shows immunomodulatory effects.

Unlike agents that target single cytokine mediators, *M. vaccae* has a wider effect through its ability to reduce several Th2 cytokines, including IL-4, IL-5 and IL-13, via immunoregulatory mechanisms including induction of regulatory T-cells that down-regulate Th2 via a mechanism involving IL-10 and T-cell growth factor (TGF)-β.

*M. vaccae* and *M. obuense* induce a complex immune response in the host. Treatment with these preparations will stimulate innate and type-1 immunity (Th1 and CD8+ CTLs) akin to what has been observed with treatment with other mycobacterial preparations (for example live attenuated BCG and mycobacterial cell wall extracts). However, a significant additional benefit of treatment with *M. vaccae* and *M. obuense*, is the regulation of the immune response through the induction of regulatory cells (T-regulatory and DC with regulatory phenotype) which control and modulate prolonged and over-exuberant immune reactions (for example, following tumour ablation). Tight control of immune reactions through immunoregulation not only limits tissue pathology but also ensures a quick return to energy efficient steady state immune equilibrium.

The present invention may be used to treat, prevent, control or inhibit a neoplastic disease. Neoplasias, tumours and cancers include a sarcoma, carcinoma, adenocarcinoma, melanoma, myeloma, blastoma, glioma, lymphoma or leukemia. Exemplary cancers include, for example, carcinoma, sarcoma, adenocarcinoma, melanoma, neural (blastoma, glioma), mesothelioma and reticuloendothelial, lymphatic or haematopoietic neoplastic disorders (e.g., myeloma, lymphoma or leukemia). In particular aspects, a neoplasm, tumour or cancer includes a lung adenocarcinoma, lung carcinoma, diffuse or interstitial gastric carcinoma, colon adenocarcinoma, prostate adenocarcinoma, esophagus carcinoma, breast carcinoma, pancreas adenocarcinoma, ovaπ an adenocarcinoma, adenocarcinoma of the adrenal gland, adenocarcinoma of the endometrium or uterine adenocarcinoma.

Neoplasia, tumours and cancers include benign, malignant, metastatic and non-metastatic types, and include any stage (I, II, III, IV or V) or grade (G1, G2, G3, etc.) of neoplasia, tumour, or cancer, or a neoplasia, tumour, cancer or metastasis that is progressing, worsening, stabilized or in remission. Cancers that may be treated according to the invention include but are not limited to cells or neoplasms of the bladder, blood, bone, bone marrow, brain, breast, colon, esophagus, gastrointestines, gum, head, kidney, liver, lung, nasopharynx, neck, ovary, prostate, skin, stomach, testis, tongue, or uterus. In addition, the cancer may specifically be of the following histological type, though it is not limited to the following: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumour, malignant; bronchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary;

acinar cell carcinoma; adenosquamous carcinoma; adenocarcinoma with squamous metaplasia; thymoma, malignant; ovarian stromal tumour, malignant; thecoma, malignant; granulosa cell tumour, malignant; androblastoma, malignant; Sertoli cell carcinoma; Leydig cell tumour, malignant; lipid cell tumour, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumour; Mullerian mixed tumour; nephroblastoma; hepatoblastoma; carcinosarcoma; mesenchymoma, malignant; Brenner tumour, malignant; phyllodes tumour, malignant; synovial sarcoma; mesothelioma, malignant; dysgerminoma; embryonal carcinoma; teratoma, malignant; struma ovarii, malignant; choriocarcinoma; mesonephroma, malignant; hemangi ° sarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumour of bone; Ewing's sarcoma; odontogenic tumour, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumour; meningioma, malignant; neurofibrosarcoma; neurilemmoma, malignant; granular cell tumour, malignant; malignant lymphoma; Hodgkin's disease; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. Preferably, the neoplastic disease may be tumours associated with a cancer selected from prostate cancer, liver cancer, renal cancer, lung cancer, breast cancer, colorectal cancer, pancreatic cancer, brain cancer, hepatocellular cancer, lymphoma, leukaemia, gastric cancer, cervical cancer, ovarian cancer, thyroid cancer, melanoma, head and neck cancer, skin cancer and soft tissue sarcoma and/or other forms of carcinoma. The tumour may be metastatic or a malignant tumour.

In an embodiment of the invention, the antimetabolite pyrimidine analogue or a pharmaceutically acceptable salt thereof, in combination therapy with an immunomodulator, is used to reduce or inhibit metastasis of a primary tumour or cancer to other sites, or the formation or establishment of metastatic tumours or cancers at other sites distal from the primary tumour or cancer thereby inhibiting or reducing tumour or cancer relapse or tumour or cancer progression.

In further embodiments, methods of the invention include, among other things, 1) reducing or inhibiting growth, proliferation, mobility or invasiveness of tumour or cancer cells that potentially or do develop metastases, 2) reducing or inhibiting formation or establishment of metastases arising from a primary tumour or cancer to one or more other sites, locations or regions distinct from the primary tumour or cancer; 3) reducing or inhibiting growth or proliferation of a metastasis at one or more other sites, locations or regions distinct from the primary tumour or cancer after a metastasis has formed or has been established, and 4) reducing or inhibiting formation or establishment of additional metastasis after the metastasis has been formed or established.

In an embodiment of the invention, administration of the antimetabolite pyrimidine analogue or a pharmaceutically acceptable salt thereof, in combination therapy with an immunomodulator, provides a detectable or measurable improvement in a condition of a given subject, such as alleviating or ameliorating one or more adverse (physical) symptoms or consequences associated with the presence of a cell proliferative or cellular hyperproliferative disorder, neoplasia, tumour or cancer, or metastasis, i.e., a therapeutic benefit or a beneficial effect.

A therapeutic benefit or beneficial effect is any objective or subjective, transient, temporary, or long-term improvement in the condition or pathology, or a reduction in onset, severity, duration or frequency of an adverse symptom associated with or caused by cell proliferation or a cellular hyperproliferative disorder such as a neoplasia, tumour or cancer, or metastasis. A satisfactory clinical endpoint of a treatment method in accordance with the invention is achieved, for example, when there is an incremental or a partial reduction in severity, duration or frequency of one or more associated pathologies, adverse symptoms or complications, or inhibition or reversal of one or more of the physiological, biochemical or cellular manifestations or characteristics of cell proliferation or a cellular hyperproliferative disorder such as a neoplasia, tumour or cancer, or metastasis. A therapeutic benefit or improvement therefore may be destruction of target proliferating cells (e.g., neoplasia, tumour or cancer, or metastasis) or ablation of one or more, most or all pathologies, adverse symptoms or complications associated with or caused by cell proliferation or the cellular hyperproliferative disorder such as a neoplasia, tumour or cancer, or metastasis. However, a therapeutic benefit or improvement need not be a cure or complete destruction of all target proliferating cells (e.g., neoplasia, tumour or cancer, or metastasis) or ablation of all pathologies, adverse symptoms or complications associated with or caused by cell proliferation or the cellular hyperproliferative disorder such as a neoplasia, tumour or cancer, or metastasis. For example, partial destruction of a tumour or cancer cell mass, or a stabilization of the tumour or cancer mass, size or cell numbers by inhibiting progression or worsening of the tumour or cancer, can reduce mortality and prolong lifespan even if only for a few days, weeks or months, even though a portion or the bulk of the tumour or cancer mass, size or cells remain.

Specific non-limiting examples of therapeutic benefit include a reduction in neoplasia, tumour or cancer, or metastasis volume (size or cell mass) or numbers of cells, inhibiting or preventing an increase in neoplasia, tumour or cancer volume (e.g., stabilizing), slowing or inhibiting neoplasia, tumour or cancer progression, worsening or metastasis, or inhibiting neoplasia, tumour or cancer proliferation, growth or metastasis.

An invention method may not take effect immediately. For example, treatment may be followed by an increase in the neoplasia, tumour or cancer cell numbers or mass, but over time eventual stabilization or reduction in tumour cell mass, size or numbers of cells in a given subject may subsequently occur.

Additional adverse symptoms and complications associated with neoplasia, tumour, cancer and metastasis that can be inhibited, reduced, decreased, delayed or prevented include, for example, nausea, lack of appetite, lethargy, pain and discomfort. Thus, a partial or complete decrease or reduction in the severity, duration or frequency of an adverse symptom or complication associated with or caused by a cellular hyperproliferative disorder, an improvement in the subjects wellbeing, such as increased energy, appetite, psychological wellbeing, are all particular non-limiting examples of therapeutic benefit.

A therapeutic benefit or improvement therefore can also include a subjective improvement in the quality of life of a treated subject. In an additional embodiment, a method prolongs or extends lifespan (survival) of the subject. In a further embodiment, a method improves the quality of life of the subject.

The terms "effective amount" or "pharmaceutically effective amount" refer to a sufficient amount of an agent to provide the desired biological, therapeutic, and/or prophylactic result. That result can be reduction, amelioration, palliation, lessening, delaying, and/or alleviation of one or more of the signs, symptoms, or causes of a disease, or any other desired alteration of a biological system. In reference to cancer, an effective amount comprises an amount sufficient to cause a tumour to shrink and/or to decrease the growth rate of the tumour (such as to suppress tumour growth) or to prevent or delay other unwanted cell proliferation. In some embodiments, an effective amount is an amount sufficient to delay development. In some embodiments, an effective amount is an amount sufficient to prevent or delay recurrence. An effective amount can be administered in one or more administrations. The effective amount of the drug or composition may: (i) reduce the number of cancer cells; (ii) reduce tumour size; (iii) inhibit, retard, slow to some extent and preferably stop cancer cell infiltration into peripheral organs; (iv) inhibit (i.e., slow to some extent and preferably stop) tumour metastasis; (v) inhibit tumour growth; (vi) prevent or delay occurrence and/or recurrence of tumour; and/or (vii) relieve to some extent one or more of the symptoms associated with the cancer.

In a most preferred embodiment, administration of the antimetabolite pyrimidine analogue or a pharmaceutically acceptable salt thereof, in combination therapy with an immunomodulator, results in a clinically relevant improvement in one or more markers of disease status and progression selected from one or more of the following: (i) overall survival, (ii): progression-free survival, (iii): overall response rate, (iv): reduction in metastatic disease, (v): circulating levels of carbohydrate antigen 19.9 (CA19.9), (vi): circulating levels of carcinembryonic antigen (CEA), (vii) nutritional status (weight, appetite, serum albumin), or (viii): pain control or analgesic use.

Pre-treatment with heat-killed whole cell *M. vaccae* and *M. obuense* gives rise to more complex immunity including not only the development of innate immunity and type-1 immunity, but also immunoregulation which more efficiently restores appropriate immune functions.

Until recently, a perceived disadvantage of chemotherapy was its suppressive effects on the immune system. More recently, some chemotherapeutic agents have been shown to enhance anti-tumour immune responses, in part by antagonizing tumour-induced immune tolerance (Ménard et al., *Cancer Immunol Immunother* 2008; 57:1579-1587). Chemotherapy, in contrast to earlier concepts, may generate beneficial immune responses, in part at least by braking tumour-induced immune tolerance.

In response to some chemotherapeutic agents (such as anthracyclines and oxaliplatin) and ionizing irradiation, tumour cells undergo immunogenic apoptosis, meaning that they trigger an immune response when they are injected subcutaneously into immunocompetent mice in the absence of any adjuvant into immunocompetent mice. In contrast, tumour cells killed as a result of treatment with other anticancer drugs (such as alkylating agents) fail to trigger such an immune reaction. A systematic comparison of the plasma membrane surface proteome of cells that undergo immunogenic as opposed to nonimmunogenic apoptosis has revealed one major difference. Only cells that undergo immunogenic apoptosis ectopically expose a protein that is normally found in the lumen of the endoplasmic reticulum (ER), namely the $Ca^{2+}$-binding chaperone calreticulin.

The terms chemotherapy and administration of a chemotherapeutic agent are interchangeable within the context of this invention.

In certain embodiments said chemotherapy comprises administration of one or more chemotherapeutic agents, preferably an antimetabolite pyrimidine analogue. Preferably the immunomodulator according to the invention is administered in combination with a chemotherapeutic agent.

In a preferred embodiment, the chemotherapeutic agent is an antimetabolite pyrimidine analogue. Such antimetabolites interfere with DNA production and therefore cell division and the growth of tumours. Antimetabolites masquerade as a purine or pyrimidine, chemicals which become the building blocks of DNA. They prevent these substances becoming incorporated into DNA during the S-phase of the cell cycle, stopping normal development and division. The chemotherapeutic agent may be selected from thymidylate synthase inhibitors such as capecitabine, Tegafur, Carmofur, floxuridine; DNA polymerase inhibitors such as cytarabine, fazarabine, sapacitabine, or valopicitabine; ribonucleotide reductase inhibitors such as gemcitabine; hypomethylating agents, such as azacitidine, decitabine or a pharmaceutically acceptable salt, solvate, hydrate, stereoisomer, clathrate, or prodrug, analogue or derivative variant of the foregoing, or combinations thereof.

In a most preferred embodiment, the chemotherapeutic agent is gemcitabine.

The term "combination" as used throughout the specification, is meant to encompass the administration of the chemotherapeutic agents in the same or separate pharmaceutical formulations, and at the same time or at different times. Thus, an immunomodulator and the chemotherapeutic agent may be provided as separate medicaments for administration at the same time or at different times. Preferably, an immunomodulator and chemotherapeutic agent are provided as separate medicaments for administration at different times. When administered separately and at different times, either an immunomodulator or chemotherapeutic agent may be administered first; however, it is preferable to administer an immunomodulator followed by chemotherapeutic agent. In addition, both drugs can be administered on the same day or at different days, and they can be administered using the same schedule or at different schedules during the treatment cycle.

The preferred duration of each cycle of chemotherapeutic agent is typically 3-4 weeks, being 4 weeks the most preferred. Multiple cycles for both drugs can be given as needed. Thus, in a particularly preferred embodiment of the invention, a treatment cycle consists of the administration of an immunomodulator weekly or fortnightly, followed by chemotherapeutic agent on day 8 and/or 15. Preferably the immunomodulator is administered after the administration of the chemotherapy.

Preferably, the immunomodulator is administered to the patient before and after administration of a chemotherapeutic agent. That is, in one embodiment, the immunomodulator is administered to the patient before and after chemotherapy.

Dose delays and/or dose reductions and schedule adjustments are performed as needed depending on individual patient tolerance to treatments.

Before and after administration of an antimetabolite pyrimidine analogue or a pharmaceutically acceptable salt thereof effective amounts of Mycohacterium may be administered in multiple (repeat) doses, for example two or more, three or more, four or more, five or more, ten or more, or twenty or more repeat doses, at intervals of about 2 weeks, or about 4 weeks or about 8 weeks.

Alternatively, the administration of am antimetabolite pyrimidine analogue or a pharmaceutically acceptable salt thereof may be performed simultaneously with the administration of the effective amounts of the *Mycobacterium*.

In a further embodiment the administration of antimetabolite pyrimidine analogue or a pharmaceutically acceptable salt thereof may be performed or administered after the administration of the effective amount of the *Mycobacterium*.

In a preferred embodiment antimetabolite pyrimidine analogue or a pharmaceutically acceptable salt thereof, is administered before the administration of the effective amount of the *Mycobacterium*.

In a most preferred embodiment, the treatment regimen comprises administration of the immunomodulator every 2 weeks for the first 3 doses followed by a rest of 4 weeks then every 2 weeks for the next 3 doses followed by every 4 weeks thereafter, with chemotherapy beginning at least 14 days after first dose of said immunomodulator, wherein administration of said chemotherapeutic antimetabolite pyrimidine analogue or a pharmaceutically acceptable salt thereof is administered intravenously at 1000 mg/m2 over 30 minutes once weekly for 3 consecutive weeks out of every 4 weeks, up to a maximum of 12 cycles (i.e. approximately 48 weeks).

The immunomodulator may be administered to the patient via the parenteral, oral, sublingual, nasal or pulmonary route. In a preferred embodiment, the immunomodulator is administered via a parenteral route selected from subcutaneous, intradermal, subdermal, intraperitoneal, intravenous and intravesicular injection. More preferably, administration by the parenteral route does not comprise intratumoural injection of mycobacterial cell wall extract.

A suitable dosage schedule according to the present invention includes administration of the immunomodulator at 2 weeks prior to and on the day of said chemotherapy, followed by further doses of said immunomodulator 2 weeks and 4 weeks later. Further doses of immunomodulator may be administered at weekly or fortnightly intervals such as at 8 weeks, 10 weeks and 12 weeks. Preferably the immunomodulator is continued to be administered at week 16 after chemotherapy and repeated every 4 weeks thereafter for up to 12 months or more following the first dose given.

The patient is who is to undergo chemotherapy according to the present invention may do so simultaneously, separately or sequentially with administration of the immunomodulator. Preferably the immunomodulator is administered to the patient prior to administration of an antimetabolite pyrimidine analogue or a pharmaceutically acceptable salt thereof. More specifically, the immunomodulator may be administered to the patient between about 4 weeks and about 1 day prior to the chemotherapy. Preferably, the immunomodulator may be administered as one or more aliquots each containing an effective amount of the immunomodulator which may be administered at one or more time intervals between 4 weeks and about 1 day prior to chemotherapy and/or the immunomodulator may be applied after administration of a chemotherapeutic agent. Even more preferably, the immunomodulator may be administered as one or more aliquots each containing an effective amount of the immunomodulator which may be administered at one or more time intervals between 4 weeks and about 1 day after the chemotherapy and/or the immunomodulator may applied after administration of a chemotherapeutic agent, and repeated on at least about 2, 4, 6, 8, 10, 12, 15, or more occasions before or after administration of a chemotherapeutic agent.

In one embodiment of the present invention, the immunomodulator may be in the form of a medicament administered to the patient in a dosage form and/or in a schedule as set out in the examples.

In an aspect of the invention, the effective amount of the immunomodulator may be administered as a single dose. Alternatively, the effective amount of the immunomodulator may be administered in multiple (repeat) doses, for example two or more, three or more, four or more, five or more, ten or more, or twenty or more repeat doses. Preferably, the immunomodulator is administered between about 4 weeks and about 1 day prior to chemotherapy, more preferably between about 4 weeks and 1 week, or about between 3 weeks and 1 week, or about between 3 weeks and 2 weeks. Administration may be presented in single or multiple doses.

A container according to the invention in certain instances, may be a vial, an ampoule, a syringe, capsule, tablet or a tube. In some cases, the mycobacteria may be lyophilized and formulated for resuspension prior to administration. However, in other cases, the mycobacteria are suspended in a volume of a pharmaceutically acceptable liquid. In some of the most preferred embodiments there is provided a container comprising a single unit dose of mycobacteria suspended in pharmaceutically acceptable carrier wherein the unit dose comprises about $1 \times 10^6$ to about $1 \times 10^{10}$ CFU of mycobacteria. In some very specific embodiments the liquid comprising suspended mycobacteria is provided in a volume of between about 0.1 ml and 10 ml, about 0.3 ml and 2 ml or about 0.5 ml and 2 ml. It will further be understood that in certain instances a composition comprising mycobacteria in a containment means is frozen (i.e. maintained at less than about zero degrees Celsius). The foregoing compositions provide ideal units for immunotherapeutic applications described herein.

Embodiments discussed in the context of a methods and/or composition of the invention may be employed with respect to any other method or composition described herein. Thus, an embodiment pertaining to one method or composition may be applied to other methods and compositions of the invention as well.

In some cases attenuated mycobacteria is administered to specific sites on or in a subject. For example, the mycobacterial compositions according to the invention, such as those comprising *M. obuense* in particular, may be administered adjacent to tumours or adjacent to lymph nodes, such as those that drain tissue surrounding a tumour. Thus, in certain instances sites administration of mycobacterial composition may be near the posterior cervical, tonsillar, axillary, inguinal, anterior cervical, sub-mandibular, sub mental or superclavicular lymph nodes. Such sites of administration may be on the right side, on the left side, or on both sides of the body. In certain very specific embodiments, mycobacterial compositions are delivered close to the axillary, cervical and/or inguinal lymph nodes. For example, a dosage of the mycobacteria may distribute into tissues adjacent to the right and left axillary lymph node and the right and left inguinal lymph nodes.

In a very specific embodiment a dosage of mycobacteria is administered to a subject by intradermal injection wherein the dosage is distributed to the axillary and inguinal on both sides of the body and wherein there are two injections (i.e. two wheals) at each site.

In some further embodiments of the invention, methods of the invention involve the administration of 2, 3, 4, 5, 6, 7, 8, 9, 10 or more doses of mycobacteria separated by a period of one day or more. In certain preferred embodiments such separate doses will be separated by several days, one week, two weeks, one month or more. For example, methods according to the invention may comprise administering 1 to 5 doses of mycobacteria over a period of three weeks or more. In yet further embodiments, methods of the invention comprise administering 1 to 5, 1 to 4, 1 to 3, 1 to 2 or 2 doses of mycobacteria over a period of about three weeks. Each dose administered may be the same or different dosage relative to a previous or subsequent dose administration. For example, in certain cases, it is preferred that a dosage of mycobacteria is lower than any dosage that was previously administered. Thus, in some specific cases, a dose of attenuated (heat-killed) mycobacteria will be administered at about half of the dosage that was administered in any previous treatment. Such methods may be preferred in certain instances where the subject's immune response to the mycobacteria is greater during subsequent therapies. Thus in certain cases, the immunomodulator may be administered a minimal number of times for example, in less than 10, 9, 8, 7, 6, 5, 4, 3 or fewer separate dosage administrations. In some cases the mycobacterial composition is administered twice. Alternatively, the immunomodulator may be administered for the length of time the cancer or tumour(s) is present in a patient or until such time the cancer has regressed or stabilized. The immunomodulator may also be continued to be administered to the patients once the cancer or tumour has regressed or stabilised.

Mycobacterial compositions according to the invention will comprise an effective amount of mycobacteria typically dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains mycobacteria will be known to those of skill in the art in light of the present disclosure, as exemplified by Remington's Pharmaceutical Sciences, 18th Ed. Mack Printing Company, 1990. Moreover, for animal (e.g., human) administration, it will be understood that preparations should meet sterility, pyrogenicity, general safety and purity standards. A specific example of a pharmacologically acceptable carrier as described herein is borate buffer or sterile saline solution (0.9% NaCl).

The preparation of an pharmaceutical composition that contains mycobacteria will be known to those of skill in the art in light of the present disclosure, as exemplified by Remington's Pharmaceutical Sciences, 18th Ed. Mack Printing Company, 1990, Moreover, for animal (e.g., human) administration, it will be understood that preparations should meet sterility, pyrogenicity, general safety and purity standards. A specific example of a pharmacologically acceptable carrier as described herein is borate buffer or sterile saline solution (0.9% NaCl).

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavouring agents, dyes, such like materials and combinations thereof, as would be known to one of ordinary skill in the art (see, for example, Remington's Pharmaceutical Sciences, 18th Ed. Mack Printing Company, 1990, pp. 1289-1329).

In a preferred embodiment, the immunomodulator is administered via a parenteral route selected from subcutaneous, intradermal, subdermal, intraperitoneal, intravenous and intravesicular injection. Intradermal injection enables delivery of an entire proportion of the mycobacterial composition to a layer of the dermis that is accessible to immune surveillance and thus capable of electing an anti cancer immune response and promoting immune cell proliferation at local lymph nodes.

Though in highly preferred embodiments of the invention mycobacterial compositions are administered by direct intradermal injection, it is also contemplated that other methods of administration may be used in some case. Thus in certain instances attenuated mycobacteria of the present invention can be administered by injection, infusion, continuous infusion, intravenously, intradermally, intraarterially, intraperitoneally, intralesionally, intravitreally, intravaginally, intrarectally, topically, intratumourally, intramuscularly, intraperitoneally, subcutaneously, subconjunctival, intravesicularlly, mucosally, intrapericardially, intraumbilically, intraocularally, orally, intracranially, intraarticularly, intraprostaticaly, intrapleurally, intratracheally, intranasally, topically, locally, inhalation (e.g. aerosol inhalation), via a catheter, via a lavage, or by other method or any combination of the forgoing as would be known to one of ordinary skill in the art (see, for example, Remington's Pharmaceutical Sciences, 18th Ed. Mack Printing Company, 1990). More preferably, administration by the parenteral route does not comprise intratumoural injection of mycobacterial cell wall extract.

All patents, patent applications, provisional applications, and publications referred to or cited herein are incorporated by reference in their entirety, including all figures and tables, to the extent they are not inconsistent with the explicit teachings of this specification. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and immunology or related fields are intended to be within the scope of the following claims.

The invention is further described with reference to the following non-limiting Example.

Example 1

Figure 2:
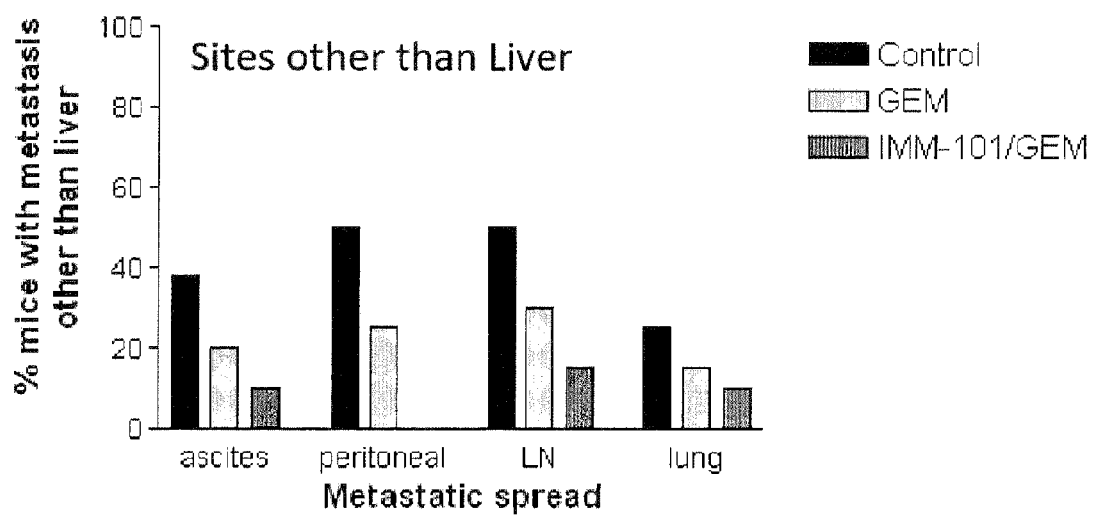
FIG. 2 shows the effect of IMM-101 with or without co-administration of gemcitabine, on metastatic spread at other peripheral sites.
Figure 3:
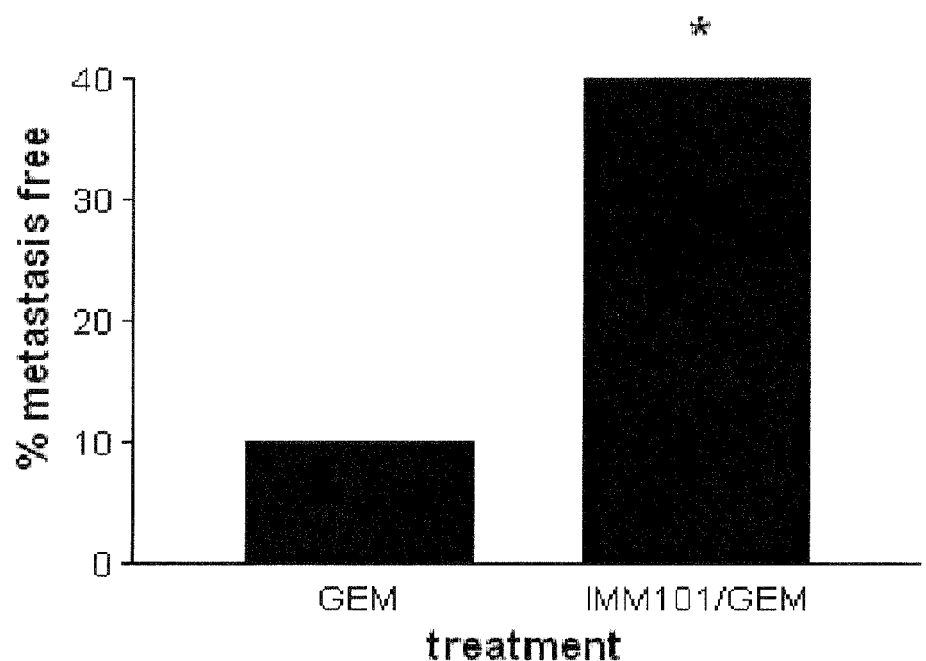
FIG. 3 shows the statistically significant improvement of IMM-101 with co-administration of gemcitabine on metastasis.

This example describes a study investigating the effect of heat-killed whole cell *M. obuense* (IMM-101) with or without administration of gemcitabine, in a genetic mouse model of pancreatic cancer. Genetically-modified mice were bred according to the method described by Hangorani et al. (*Cancer Cell; May* 2005; Vol. 7: 469-483), and tested according to the following protocol:

8 mice untreated (control)
    20 mice treated with 100 mg/kg Gemcitabine i.p. (Q3dx4; day 0, 3, 6, 9 ONLY)
    20 mice treated with Gemcitabine and IMM101;

Dose: 0.1 mg/mouse in 100 microliter borate buffer
Schedule: on alternating days over 5 day period with 2 day break for the length of the study (day 1, 3, 5, 8, 10, 12, 15. etc);
Route: s.c. alternating in the scruff of the neck and at the base of the tail
8 mice treated with IMM-101 only The combination therapy did reduce metastatic spread in the liver (see FIG. 2) and other peripheral sites (see FIG. 3). The combination of gemcitabine with IM-101 significantly and statistically reduced the occurrence of metastasis.

Example 2

A study to compare, in patients with advanced pancreatic cancer, the effects of gemcitabine (GEM) in combination with IMM-101 (a suspension of heat-killed whole cell *M. obuense* in borate-buffered saline) to gemcitabine alone on:
Safety and tolerability, including QoL.
Clinical signs and symptoms of disease.
Overall survival (OS), progression-free survival (PFS), and overall response rate (ORR).
Selected markers of tumour burden and immunological status
Disease outcome Patients, who provided informed consent, participated in a screening period of up to 28 days to establish eligibility. Once eligibility was confirmed, patients were randomised (2:1) to receive either:
Chemotherapy (GEM) with IMM-101 (active group) or,
Chemotherapy (GEM) alone (control group)

Randomisation was stratified by baseline World Health Organisation (WHO) performance status (0-1 vs. 2) and extent of disease (locally advanced inoperable vs. metastatic [irrespective of primary tumour] vs. disseminated peritoneal disease vs. any combination of these). The patient then entered the Treatment Phase of the study.

The combination treatment regimen comprised administration of a single 0.1 ml intradermal injection of IMM-101 into the skin overlying the deltoid muscle, with the arm being alternated between each dose, every 2 weeks for the first 3 doses followed by a rest of 4 weeks then every 2 weeks for the next 3 doses followed by every 4 weeks thereafter, with chemotherapy beginning at least 14 days after first dose of IMM-101, wherein administration of gemcitabine was administered intravenously at 1000 mg/ml over 30 minutes once weekly for 3 consecutive weeks out of every 4 weeks, up to a maximum of 12 cycles (i.e. approximately 48 weeks). The active comparator arm received the normal standard of care—up to 12 cycles of gemcitabine. Dosing of gemcitabine was as per the normal prescribing information for pancreatic cancer.

The combination therapy results in a clinically relevant improvement in one or more markers of disease status and progression, selected from one or more of the following: (i) overall survival, (ii): progression-free survival, (iii): overall response rate, (iv): reduction in metastatic disease, (v): circulating levels of carbohydrate antigen 19.9 (CA19.9), (vi): circulating levels of carcinoembryonic antigen (CEA), (vii) nutritional status (weight, appetite, serum albumin), or (viii): pain control or analgesic use.

REFERENCES

Apetoh L, Ghiringhelli F, Tesniere A, et al. Cancer is not just a disease of a tissue: it is a host disease. How to reactivate host defense against tumours using conventional therapies of cancer? *Ann Endocrinol* (Paris) 2008a; 69:151-152.

Apetoh L, Tesniere A, Ghiringhelli F, et al. Molecular interactions between dying tumour cells and the innate immune system determine the efficacy of conventional anticancer therapies. *Cancer Res* 2008b; 68:4026-30.

Dunn G P, Old L J, Schreiber R D. The three Es of cancer immunoediting. *Annu Rev Immunol* 2004; 22:329-360.

Dvorak H F. Tumours: wounds that do not heal. Similarities between tumour stroma generation and wound healing. *N Engl J Med* 1986; 315:1650-1659.

Ladoire S, Arnould L, Apetoh L, et al. Pathologic complete response to neoadjuvant chemotherapy of breast carcinoma is associated with the disappearance of tumour-infiltrating foxp3+ regulatory T cells. *Clin Cancer Res* 2008; 14:2413-2420.

Locher C, Conforti R, Aymeric L, et al. Desirable cell death during anticancer chemotherapy. *Ann N Y Acad Sci* 2010; 1209:99-108.

Ménard C, Martin F, Apetoh L, et al. Cancer chemotherapy: not only a direct cytotoxic effect, but also an adjuvant for antitumour immunity. *Cancer Immunol Immunother* 2008; 57:1579-1587.

Tesniere A, Panaretakis T, Kepp O, et al. Molecular characteristics of immunogenic cancer cell death. *Cell Death Differ* 2008; 15:3-12.

Tesniere A, Apetoh L, Ghiringhelli F, et al. Immunogenic cancer cell death: a key-lock paradigm. *Curr Opin Immunol* 2008; 20:504-511.

Vakkila J, Lotze M T. Inflammation and necrosis promote tumour growth. *Nat Rev Immunol* 2004; 4: 641-648.

Zeh H J, Lotze M T. Addicted to death: invasive cancer and the immune response to unscheduled cell death. *J Immunother* 2005; 28:1-9.

Zitvogel L, Casares N, Pequignot M O, et al. Immune response against dying tumour cells. *Adv Immunol* 2004; 84: 131-179.

Zitvogel L, Apetoh L, Ghiringhelli F, et al. The anticancer immune response: indispensable for therapeutic success? *J Clin Invest* 2008; 118:1991-2001.

What is claimed is:

1. A method of preventing, treating, reducing, inhibiting and/or controlling the formation or establishment of metastasis of a primary neoplasia, tumour or cancer at one or more sites distinct from a primary neoplasia, tumour or cancer, in a subject intended to undergo chemotherapy, wherein said method comprises simultaneously, separately or sequentially administering to the subject, a therapeutically effective amount of (i) gemcitabine or a pharmaceutically acceptable salt, solvate, hydrate, stereoisomer, clathrate, or prodrug thereof; and (ii) an immunomodulator, comprising a whole cell *Mycobacterium obuense*; wherein the metastasis is associated with pancreatic cancer.

2. The method according to claim 1, wherein the *Mycobacterium obuense* is a non-pathogenic heat-killed *Mycobacterium obuense*.

3. The method according to claim 2, wherein the non-pathogenic heat-killed *Mycobacterium obuense* is the rough variant.

4. The method according to claim 2, wherein the non-pathogenic heat-killed *Mycobacterium obuense* is administered via the parenteral, oral, sublingual, nasal or pulmonary route.

5. The method according to claim 4, wherein the parenteral route is selected from subcutaneous, intradermal, subdermal, intraperitonal, intravenous, or intravesicular injection.

6. The method according to claim 4, wherein the parenteral route does not comprise intratumoural injection.

7. The method according to claim 2, wherein the effective amount of non-pathogenic heat-killed *Mycobacterium obuense* is from $10^7$ to $10^9$ cells.

8. The method according to claim 1, wherein administration of said immunomodulator is prior to administration of gemcitabine or a pharmaceutically acceptable salt, solvate, hydrate, stereoisomer, clathrate, or prodrug thereof.

9. The method according to claim 8, wherein administration of said immunomodulator is between 4 weeks and 1 day prior to and/or after the administration of gemcitabine or a pharmaceutically acceptable salt, solvate, hydrate, stereoisomer, clathrate, or prodrug thereof.

10. The method according to claim 9, wherein said administration of immunomodulator comprises administration of one or more aliquots of an effective amount administered at one or more time intervals between 4 weeks and 1 day prior to and/or after the administration of a therapeutically effective amount of gemcitabine or a pharmaceutically acceptable salt, solvate, hydrate, stereoisomer, clathrate, or prodrug thereof; preferably wherein administration of the immunomodulator is before and continues after the administration of a therapeutically effective amount of said antimetabolite pyrimidine gemcitabine or a pharmaceutically acceptable salt, solvate, hydrate, stereoisomer, clathrate, or prodrug thereof.

11. The method according to claim 1, wherein a therapeutically effective amount of gemcitabine or a pharmaceutically acceptable salt thereof is administered to the subject.

* * * * *

UNITED STATES PATENT AND TRADEMARK OFFICE
CERTIFICATE OF CORRECTION

PATENT NO. : 8,617,520 B2  
APPLICATION NO. : 13/396866  
DATED : December 31, 2013  
INVENTOR(S) : Charles Akle, Satvinder Mudan and John Grange It is certified that error appears in the above-identified patent and that said Letters Patent is hereby corrected as shown below:

In the Claims:

Column 17,
Lines 24-25, "of said antimetabolite pyrimidine gemcitabine" should read --of gemcitabine--

Signed and Sealed this
Twenty-ninth Day of April, 2014

Michelle K. Lee
*Deputy Director of the United States Patent and Trademark Office*